(12) United States Patent
Bach et al.

(10) Patent No.: US 7,041,289 B1
(45) Date of Patent: May 9, 2006

(54) METHOD FOR TREATING ESTABLISHED SPONTANEOUS AUTO-IMMUNE DISEASES IN MAMMALS

(75) Inventors: Jean-Francois Bach, Paris (FR); Lucienne Chatenoud, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 589 days.

(21) Appl. No.: 08/986,568

(22) Filed: Dec. 5, 1997

(51) Int. Cl.
*A61K 39/395* (2006.01)

(52) U.S. Cl. .............................. 424/133.1; 424/144.1; 424/154.1; 424/173.1; 424/810; 530/868

(58) Field of Classification Search ............. 424/133.1, 424/154.1, 144.1, 173.1, 810; 530/387.3, 530/388.75, 389.6, 860, 868
See application file for complete search history.

(56) References Cited

OTHER PUBLICATIONS

Racadot, E et al. Clinical Immunotherapy. 1(3):199-208, May 1994.*
Gussow et al. Methods in Enzymology. 203:99-121, 1991.*
Beers et al (Eds.), The Merck Manual, Seventeenth Edition, Merck Research Laboratories, 1999, pp. 816-818.*
Chatenoud et al., "CD3 Antibody-Induced Dominant Self Tolerance in Overtly Diabetic NOD Mice", The Journal of Immunology, The American Association for Immunologists, pp. 2947-2954 (1997).
Hirsch et al., "Anti-CD3 F(ab')$_2$ Fragments are Immunosuppressive in Vivo Without Evoking Either the Strong Humoral Response or Morbidity Associated with Whole mAb" *Transplantation* 49:1117-1123 (1990).
Hirsch et al., "Differential T Cell Hyporesponsiveness Induced by In Vivo Administration of Intact or F(ab')$_2$ Fragments of Anti-CD3 Monoclonal Antibody" *The Journal of Immunology* 147:2088-2093 (1991).
Herold et al., Prevention of Autoimmune Diabetes with Nonactivating Anti-CD3 Monoclonal Antibody *Diabetes* 41:385-391 (1992).
Hughes et al., "Induction of Helper Cell Hyporesponsiveness in an Experimenthal Model of Autoimmunity by Using Nonmitogenic Anti-CD3 Monoclonal Antibody" *J. Immunol.* 153(7):3319-3325 (1994).
Chatenoud et al., "Anti-CD3 antibody induces long-term remission of overt autoimmunity in nonobese diabetic mice" *Proc. Natl. Acad. Sci. USA* 91:123:127 (1994).
Johnson et al., "Use of Anti-CD3ε F(ab')$_2$ Fragments In Vivo to Modulate Graft-Versus-Host Disease Without Loss of Graft-Versus-Leukemia Reactivity After MHC-Matched Bone Marrow Transplantation," *J. Immunol.* 154(10):5542-5554 (1995).
Chatenoud, et al., "Monoclonal Antibodies to CD3 Restore Self Tolerance in Overtly Diabetic NOD Mice: Both Mitogenic and Non-Mitogenic Antibodies Afford Tolerance," *Autoimmunity*, 21:72, Abstract A276 (1995).

* cited by examiner

*Primary Examiner*—David Saunders
(74) *Attorney, Agent, or Firm*—Elliot M. Olstein; Raymond J. Lillie

(57) ABSTRACT

A method of treating spontaneous and ongoing auto-immune diseases in mammals, comprising administering to a mammal, in need of such a treatment, a therapeutically effective amount of one or more non mitogenic anti-CD3 active principles to achieve permanent disease remission through the induction of antigen-specific unresponsiveness, i.e. immune tolerance.

10 Claims, 1 Drawing Sheet

METHOD FOR TREATING ESTABLISHED SPONTANEOUS AUTO-IMMUNE DISEASES IN MAMMALS

Figure 1A:
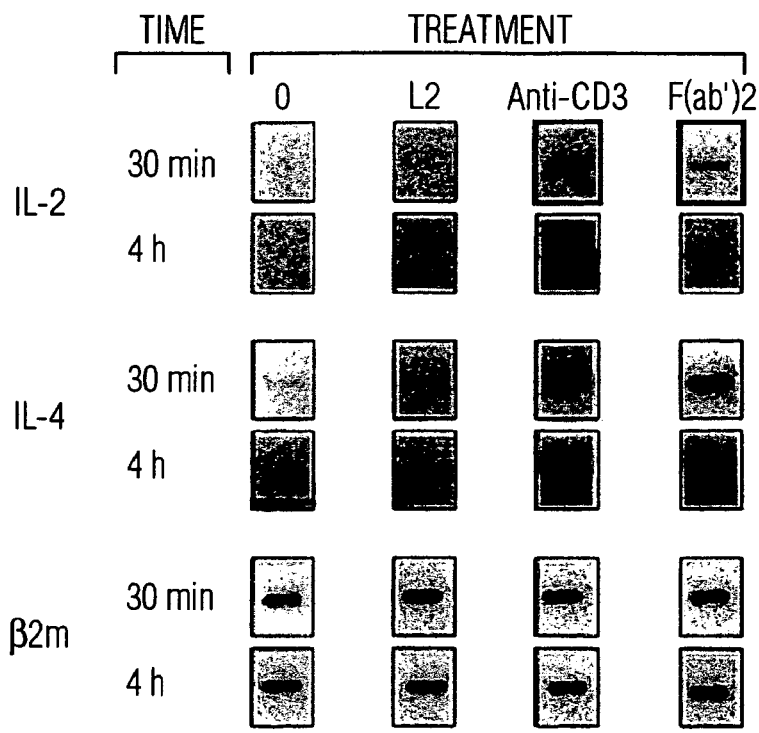

The invention relates to a method for treating established and ongoing spontaneous auto-immune diseases in mammals.

In order to suppress T cell function, immunotherapy based on the use of antibodies directed at T cell surface receptors, particularly of monoclonal antibodies (mAbs), has been extensively investigated. Particularly, mAbs directed against the CD3 complex of the T cell receptor have been shown to cause transient T-cell depletion and antigenic modulation of the CD3-T cell receptor complex.

In PNAS USA, vol. 91, p 123–127, 1994 Immunology, the inventors, with other co-authors, have reported that a short term treatment with low doses of an anti-CD3 mAb could restore self tolerance to β-cell-associated antigens, thus inducing complete and durable remission of the spontaneous auto-immune diabetes, in overtly diabetic NOD (non obese diabetic) mice.

By further investigating the mode of action of anti-CD3 mAb in this model, the inventors have found that the long term effect was obtained only when treating animal at a very advanced disease stage, i.e. overt auto-immunity. They also demonstrate that non mitogenic, $F(ab')_2$ fragments of the entire CD3 mAb, that are much better tolerated than the whole entire CD3-mAb, also afford a long term in vivo effect in overtly diabetic NOD mice as did the whole anti-CD3 mAb.

This finding is an unexpected extension of the published data which until now, in both transplantation and antigen and/or pharmacologically induced auto-immunity, has proposed $(Fab')_2$ fragments of anti-CD3 mAb as effective tools to only achieve immunosuppression (an overall depression of immune responses that is only maintained through the chronic administration of the drugs), but not to promote permanent antigen-specific unresponsiveness namely, a state of immune tolerance (an antigen-specific immune unresponsiveness that is maintained in the absence of chronic generalized immunosuppression).

Such results are useful for application to other auto-immune situations where similar immunoregulatory mechanisms, such as those present in auto-immune diabetes, have been observed.

Accordingly, an object of the invention is to provide a method of treatment of spontaneous and ongoing of auto-immune diseases in mammals to achieve permanent Ag-specific unresponsiveness, without the morbidity and with a minimal humoral response as that encountered when administering the whole mitogenic antibody.

Another object of the invention is to provide effective tools useful for such a method of treatment.

According to the invention, the method of treating auto-immune diseases in mammals comprises administering to a mammal, in need of such a treatment, a therapeutically effective amount of one or more non mitogenic anti-CD3 active principles to achieve permanent disease remission through the induction of antigen-specific unresponsiveness, i.e. immune tolerance.

Such a treatment was shown to be able to promote durable remission of the established disease without the clinical side effects involved when administering mitogenic whole anti-CD3 antibodies.

Particularly preferred non mitogenic anti-CD3 antibodies are monoclonal antibodies or fragments thereof, especially $F(ab')_2$ fragments.

Said fragments are advantageously such as obtained by pepsin digestion of the whole antibody.

In view of their therapeutical use, said active principle(s) are highly purified and particularly endotoxin-free.

Said non mitogenic anti-CD3 monoclonal antibody, or fragment thereof is of murine origin or is an humanized antibody.

The permanent antigen-specific unresponsiveness obtained with said anti-CD3 active principles make them particularly useful as therapeutic tools for treating auto-immune pathologies. In particular, they are suitable for treating diabetes, rheumatoid arthritis, multiple sclerosis or psoriasis.

In said applications, they will be administered, if desired, in combination with other active ingredients and/or compounds which facilitate their assimilation.

Said therapeutical tools are advantageously administered in combination with pharmaceutical carriers under the form of pharmaceutical preparations.

Different forms of administration may be used, especially for injectable route.

The injectable forms contain 5 to 20 mg of active principle per unit dose, preferably from 5 to 10 mg.

For information only, the dose which can be used in the treatment of auto-immune diseases in humans, for example diabetes, is 5 to 10 mg/day for 10 to 14 consecutive doses.

Figure 1B:
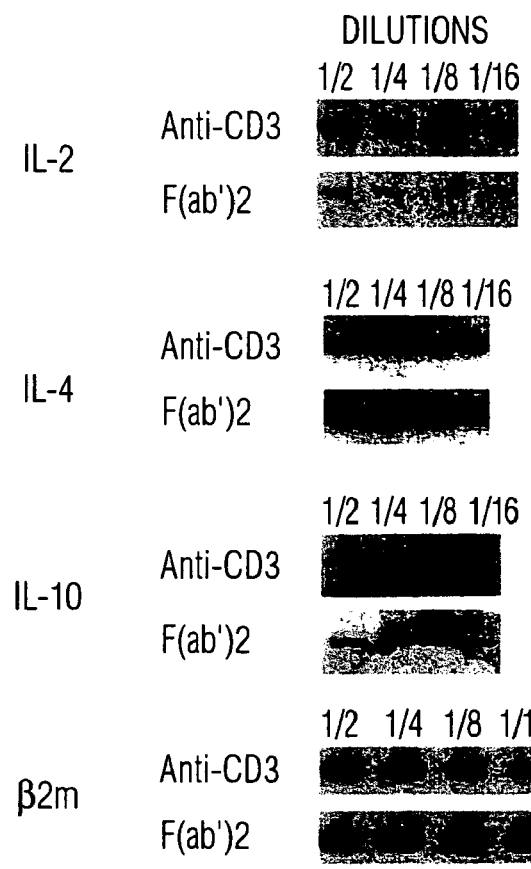

The invention now will be described with respect to the drawings, wherein:

FIG. 1A shows the kinetics of expression of Interleukin-2 (IL-2), Interleukin-4 (IL-4), and β-2 microglobulin (β-2 m) RNA in NOD female mice that were given intact CD3 monoclonal antibody, $F(ab')_2$ fragments of CD3 monoclonal antibody, L2 antibody, or saline; and FIG. 1B shows the results of semiquantification of amplification products using doubling dilutions of cDNA for PCR reactions for IL-2, IL4, and IL-10.

Other characteristics and advantages of the invention will appear from the examples given hereinbelow.

EXAMPLE 1

Treatment of overtly diabetic NOD female mice with purified $F(ab')_2$ fragments of CD3 anti-mAb.

NOD mice ($K^d$, I-A$^{NOD}$, $D^b$) were bred under specific pathogen-free conditions; in females, spontaneous IDDM appears by 14 weeks of age (90% incidence at 30 weeks of age) and is preceded by insulitis at 4 to 6 weeks.

In a preferred embodiment of the invention said non mitogenic anti-CD3 active principle is a non mitogenic anti-CD3 antibody or a fragment thereof. Such fragments are advantageously $F(ab')_2$ fragments.

The cell line producing the hamster 1452C11 mAb (IgG, anti-mouse CD3 ε-chain) was used in those experiments (O. M. Les et al, 1987, PNAS USA 84:1374).

The anti-CD3 mAb $F(ab')_2$ fragments were prepared by pepsin digestion.

Pepsin (Sigma Chemical Co., St. Louis, Mo.) was used at a final concentration of 2% (20 μg/mg of purified antibody) in 1M acetate buffer, pH 3. Digestion was conducted for 2 h at 37° C. Following dialysis at 4° C. using 0.1 M PBS pH 8, digested $F(ab')_2$ fragments were purified in two steps: a protein A-Sepharose CL-4B affinity chromatography column to eliminate digested Fc fragments, then gel filtration of the nonretained fraction on an Ultragel AcA54 column (Pharmacia, Uppsala, Sweden).

The physico-chemical properties of the fragment preparations were analyzed by SDS-PAGE.

The binding capacity was tested by immunofluorescence in a classical competition assay using purified FITC-labeled whole CD3 mAb.

The digestion and purification of F(ab')$_2$ fragments was performed with special caution to avoid endotoxin contamination. The material used for in vivo treatment was negative in the Limulus assay.

NOD females presenting with overt diabetes were included in the treatment protocol when a fasting glycemia ranging 3.5 to 4 g/L was scored on two consecutive occasions. Mice were then randomized to receive a treatment with CD3 mAb F(ab')$_2$ fragments (50 µg/day for 5 consecutive days), whole CD3mAb (5–20 µg/day for 5 consecutive days), or as a control normal hamster Igs.

Complete remission was defined as a return to normal glycemia and the disappearance of glycosuria in the absence of any exogenous insulin supply. Histopathology on paraffin sections of Bovin-fixed or frozen pancreatic tissue were performed as previously described (1). Scoring of mononuclear cell infiltration was as follows: grade 0=normal islets; grade 1=focal or peripheral insulitis (lymphocytes around the islet, but no destruction of endocrine cells as assessed by labeling with anti-insulin Abs); and grade 2=invasive destructive insulitis.

The results regarding the remission of overt diabetes in the mice following the short treatment with purified F(ab')$_2$ fragments are given in Table 1.

TABLE I

| Weeks After Treatment | % Remission of IDDM | |
| --- | --- | --- |
|  | Anti-CD3 F(ab')$_3$ n = 42 | Hamster 1 g n = 18 |
| 0 | 0 | 0 |
| 2 | 55 | 22 |
| 4 | 62 | 16 |
| 6 | 64 | 0 |
| 10 | 67 | 0 |
| 20 | 67 | 0 |

The difference in percent remission between CD3 mAB F(ab')$_2$ fragments-treated and control animals is statistically significant (p<0.01) using $_N$test.

As shown by said results, F(ab')$_2$ fragments of the mAb appeared potent in promoting permanent remission of overt diabetes in the conditions of the experiments.

EXAMPLE 2

Study of the triggering effect of F(ab')$_2$ fragments of CD3 mAb on cytokine gene transcription.

NOD females received a single i.v. injection of either intact 145 2C11 CD3 mAb (20 µg) or purified F(ab')$_2$ fragments of 145 2C11 CD3 mAb (50 µg). Mice injected with saline or with 5 to 50 µg of L2, a hamster mAb specific for recombinant but not natural mouse IL-2, were used as controls. Three individual animals were analyzed in each group. Spleen cells were collected before any treatment and at various times following injection of the different preparations, and RNA was extracted for RT-PCR.

Crude RNA was extracted using TRIzol (Life Technologies) followed by isopropanol precipitation. For reverse transcription (RT), total RNA (6 µl in a final volume of 12 µl) was added to 18 µl of cDNA synthesis reaction mixture. Two microliters of RT product was amplified using PCR for 30 cycles. final volume of 50 µl, with standard buffer conditions and a final Mg$^{2+}$ concentration of 1.5 mM (2.5 U Taq UNA polymerase, Life Technologies). Each PCR cycle consisted of 1 min at 94° C., 1 min at 55° C., and 1 min at 72° C. on a Techne thermal cycler (Osi, Paris, France); 100 ng of cDNA was used for PCR unless stated otherwise. When needed to semi-quantitate the amplification products obtained, PCR with doubling dilutions of cDNA was performed. The following primers (Bioprobe Systems, France) were used: IFN-γ 5' primer, CCA GCA GAG AAT GGA AAG TC; IFN-γ 3' primer. GAT GCT GCT TAC ATG TCT CG; IL.2 5' primer CCA GCA GAG AAT GGA AAG TC; IL-2 3' primer, GAT GCT GCT TAC ATG TCT CG; IL-4 5' primer. TCG GCA TTT TGA ACG AGG TC, IL-4 3' primer. GAA AAG CCC GAA AGA GTC TC; IL-10 5' primer, GGG ATG ACA GTA GGG GAA CC; IL-10 3' primer, AGA GCA AGG CAG TGG AGC AG: β$_2$-microglobulin 5' primer, CCA GCA GAG AAT GGA AAG TC β$_2$-microglobulin 3' primer, GAT GCT GCT TAC ATG TCT CG. Ten microliters of RT-PCR products were separated by 1.2% agarose gel electrophoresis in 1×TBE (Tris-borate-EDTA) containing 0.2 µg/ml of ethidium bromide and visualized under UV light. Where products were semiquantified, RT-PCR, β2 microglobulin mRNA was used as a housekeeping reporter gene.

The kinetics of mRNA expression is shown in FIG. 1, part A. Semiquantification of amplification products was performed using doubling dilutions of cDNA for PCR reactions; data are shown for IL-2, IL-4, and IL-10 in FIG. 1, part B.

As shown in FIG. 1A, using PCR on splenocytes from anti-CD3 F(ab')$_2$-treated animals, enables identification of the transcription of mRNAs specific for IL-2, IL-4, IL-10, and IFN-γ. Semiquantification using serial dilution of cDNA samples suggested that, as compared with what was observed in NOD mice treated with intact CD3 mAb, F(ab')$_2$ fragments promote a less effective transcription of IL-2 mRNA, whereas similar levels of IL-4, II-10, and IFN-γ message were detected (FIG. 1B).

EXAMPLE 3

Cytokine production by stimulated spleen cells from CD3 mAb- and F(ab')$_2$-treated NOD mice.

Spleen cells from CD3 mAb- and F(ab')$_2$—treated NOD mice were collected at different times after treatment and tested for their capacity to secrete IFN-γ and IL-4 upon mitogenic stimulation using Con A.

Spleen cells from CD3 or F(ab')$_2$ fragments-treated animals were collected and cultured in vitro (1×10°/ml) in 24-well plates, for 24 to 48 h in a humidified atmosphere containing 5% CO$_2$, in DMEM-Glu- tamax (Life Technologies, Paisley, Scotland) supplemented with 100 IU/ml penicillin, 100 µg/ml streptomycin, sodium pyruvate, nonessential aminoacids, 0.05 mM β-mercaptoethanol, and 10% FCS. In stimulated cultures, Con A was added at a final concentration of 10 µg/ml. Supernatants were collected and stored frozen at −80° C. until tested. IFN-γ and IL-4 were quantitated using specific ELISA as already described (17). The Abs used for detection were AN18 (kindly provided by Dr. A. O'Garra, DNAX, Palo Alto, Calif.) and biotinylated R46A2 for IFN-γ and 11B11 and biotinylated BVD6 (kindly provided by A. O'Garra) for IL-4, Mouse rIL-4 (R&D Systems. Minneapolis, Minn.) and IFN-γ were used as internal standards. Detection limits were 0.2 ng/ml for IL-4 and 0.1 ng/ml for IFN-γ.

The results are given in Table 2

TABLE 2

| Treatment | Time from Treatment (week) | IFN-γ (ng/ml) |
|---|---|---|
| Anti-CD3 | 2 | 68.36 ± 11.51* |
| Anti-CD3 F(ab')$_2$ | 2 | 16.37 ± 3.40* |
| Hamster Ig | 2 | 101.90 ± 13.34* |
| Anti-CD3 | 7 | 31.74 ± 4.14[5] |
| Anti-CD3 F(ab')$_2$ | 7 | 23.21 ± 5.69[1] |
| Hamster Ig | 7 | 35.76 ± 4.20 |
| Untreated controls |  | 29.42 ± 7.11 |

As compared with age-matched controls injected with irrelevant hamster Ig, polyclonally activated spleen cells from CD3 mAb- and F(ab')$_2$ fragment-related NOD mice showed, for about 5 wk from the end of treatment, a significantly decreased IFN-γ-producing ability (Table II).

EXAMPLE 4

Pharmaceutical Formulation

The active principles are formulated under a desaggregated form and either lyophilyzed or suspended into an appropriate liquid, each dose containing, as above mentioned, 5 to 20 mg of non mitogenic antibody or a fragment thereof.

What is claimed is:

1. A method of treating an ongoing autoimmune disease in a human having said disease, wherein said disease is diabetes, comprising:
treating said human by administering one or more non-mitogenic anti-CD3 active compounds selected from the group consisting of CD3 antibodies and fragments of CD3 antibodies in an amount effective to treat said diabetes.

2. The method of claim 1 wherein said treatment results in a durable remission of said diabetes.

3. The method of claim 1 wherein said administration of said one or more non-mitogenic anti-CD3 active compounds is a non-chronic administration.

4. The method of claim 1 wherein said non-mitogenic anti-CD3 active compound is a non-mitogenic anti-CD3 monoclonal antibody (Fab')$_2$ fragment.

5. The method of claim 1 wherein said non-mitogenic anti-CD3 active compound is a non-mitogenic anti-CD3 antibody.

6. The method of claim 5 wherein said non-mitogenic anti-CD3 active compound is a non-mitogenic anti-CD3 monoclonal antibody.

7. The method of claim 6 wherein said monoclonal antibody is selected from the group consisting of murine or humanized antibody.

8. The method of claim 1 wherein said compound is highly purified and endotoxin-free.

9. The method of claim 1 wherein said active compound is administered by injection.

10. The method of claim 1 wherein said non-mitogenic anti-CD3 active compound is administered in an injectable form that contains from 5 to 20 mg of the non-mitogenic anti CD3 active compound.

* * * * *